(12) United States Patent
Lee et al.

(10) Patent No.: US 7,867,392 B2
(45) Date of Patent: Jan. 11, 2011

(54) MAGNETIC CARRIER AND MEMBRANE BIOREACTOR COMPRISING ENZYME FOR INHIBITING BIOFILM FORMATION

(75) Inventors: Chung-Hak Lee, Seoul (KR); Kyung-Min Yeon, Seoul (KR)

(73) Assignee: SNU R&DB Foundation, Seoul (KR)

( * ) Notice: Subject to any disclaimer, the term of this patent is extended or adjusted under 35 U.S.C. 154(b) by 268 days.

(21) Appl. No.: 12/272,333

(22) Filed: Nov. 17, 2008

(65) Prior Publication Data

US 2009/0159533 A1    Jun. 25, 2009

(30) Foreign Application Priority Data

Dec. 24, 2007   (KR) ................. 10-2007-0136932

(51) Int. Cl.
    *B01D 35/06*   (2006.01)
(52) U.S. Cl. ...................... 210/222; 210/263
(58) Field of Classification Search ............ 210/222, 210/263, 606
    See application file for complete search history.

(56) References Cited

U.S. PATENT DOCUMENTS 6,777,223 B2   8/2004   Xu

2009/0324574 A1 *  12/2009  Mathur et al. .............. 424/94.6

FOREIGN PATENT DOCUMENTS

| JP | 02-229545 | 9/1990 |
|---|---|---|
| JP | 07-108292 | 4/1995 |

OTHER PUBLICATIONS

Yeon et al., "Correlation between Biofueling and Quorum Sensing in Membrane Bioreactor," *Korean Society on Water Quality & Korean Society of Water and Wastewater* (2006). English Abstract Only.
Camara et al., "Controlling infection by tuning in and turning down the volume of bacterial small-talk." *The Lancet—Infectious Diseases* 2(2002): 667-676.
Fuqua et al., "Census and consensus in bacterial ecosystems: The LuxR-LuxI family of quorum-sensing transcriptional regulators." *The Annu. Rev. Microbiol.* 50(1996): 727-751.
Davies et al., "The involvement of cell-to-cell signals in the development of a bacterial biofilm." *Science* 280:295(1998): 294-298.
Baveja et al., "Furanones as potential anti-bacterial coatings on biomaterials." *Biomaterials* 25(2004): 5003-5012.

(Continued)

*Primary Examiner*—Chester T Barry
(74) *Attorney, Agent, or Firm*—Merchant & Gould P.C.

(57) ABSTRACT

A technique for inhibiting biofouling caused by biofilms grown on a material surface of a water system where microorganisms exist such as the membrane surface of a membrane bioreactor (MBR) for advanced wastewater treatment is disclosed. Specifically, a magnetic carrier comprising an enzyme for quenching quorum sensing that inhibits biofilm formation, a membrane bioreactor system that can be stably operated without inactivation and loss of enzymes and a method for inhibiting biofilm formation are described.

10 Claims, 11 Drawing Sheets

OTHER PUBLICATIONS

Dong et al., "Quenching quorum-sensing-dependent bacterial infection by an N-acyl homoserine lactonase." *Letters to Nature* 411(2001): 813-817.

Hentzer et al., "Attenuation of *Pseudomonas aeruginosa* virulence by quorum sensing inhibitors." *The EMBO Journal* 22: 15(2003): 3803-3815.

Chang et al., "Membrane filtration characteristics in membrane-coupled activated sludge system—the effect of physiological states of activated sludge on membrane fouling." *Desalination* 120(1998): 221-233.

Hanft, Susan, "Business opportunity report—C-240—Membrane bioreactors in the changing world water market." *Business Communications Company, Inc.* (2006).

Kim et al., "Biofilm structure and extracellular polymeric substances in low and high dissolved oxygen membrane bioreactors." *Separation Science & Technology* 41(2006): 1213-1230.

Yeon et al., "Quorum quenching techniques for the performance enhancement of the membrane bioreactor." (Nov. 21, 2007).

* cited by examiner

MAGNETIC CARRIER AND MEMBRANE BIOREACTOR COMPRISING ENZYME FOR INHIBITING BIOFILM FORMATION

CROSS-REFERENCE TO RELATED APPLICATION

This application claims under 35 U.S.C §119(a) the benefit of Korean Patent Application No. 10-2007-136932 filed Dec. 24, 2007, the entire contents of which are incorporated herein by reference.

BACKGROUND OF THE INVENTION

The present invention generally relates to a technique for inhibiting formation of biofilm or microorganic slime in equipment or facility of a water system where microorganisms exist, such as biofilm on the membrane surface which cause membrane biofouling during the operation of a membrane bioreactor (MBR) for advanced wastewater treatment. More specifically, the present invention relates to a technique for operating a MBR process stably and efficiently without inactivation and loss of enzymes using a specific magnetic carrier that comprises an enzyme for inhibiting biofilm formation (e.g., enzyme for quenching quorum sensing) immobilized thereon.

Recently, a MBR process which is a new type of wastewater treatment process combining a membrane separation process with a biological wastewater treatment reactor (bioreactor) has been actively researched as an alternative to conventional physical/chemical or biological wastewater treatment process, and applied in an actual process. Since the MBR process requires less space in comparison with the conventional physical/chemical or biological wastewater treatment process, the MBR process is more economical. Moreover, the MBR process can be operated stably and efficiently even under sudden external load so as to secure high quality of treated water and to reduce sludge production. Currently, there are about 4,000 plants for operating the MBR process around the world. The market size is about US $216,600,000 in 2005, and the average growth rate is expected to be 10.9% annually until 2010 (The Market Survey Report in 2005, Business Communication Company, Inc.). Therefore, the distribution and research for MBR process have been made actively.

Figure 1:
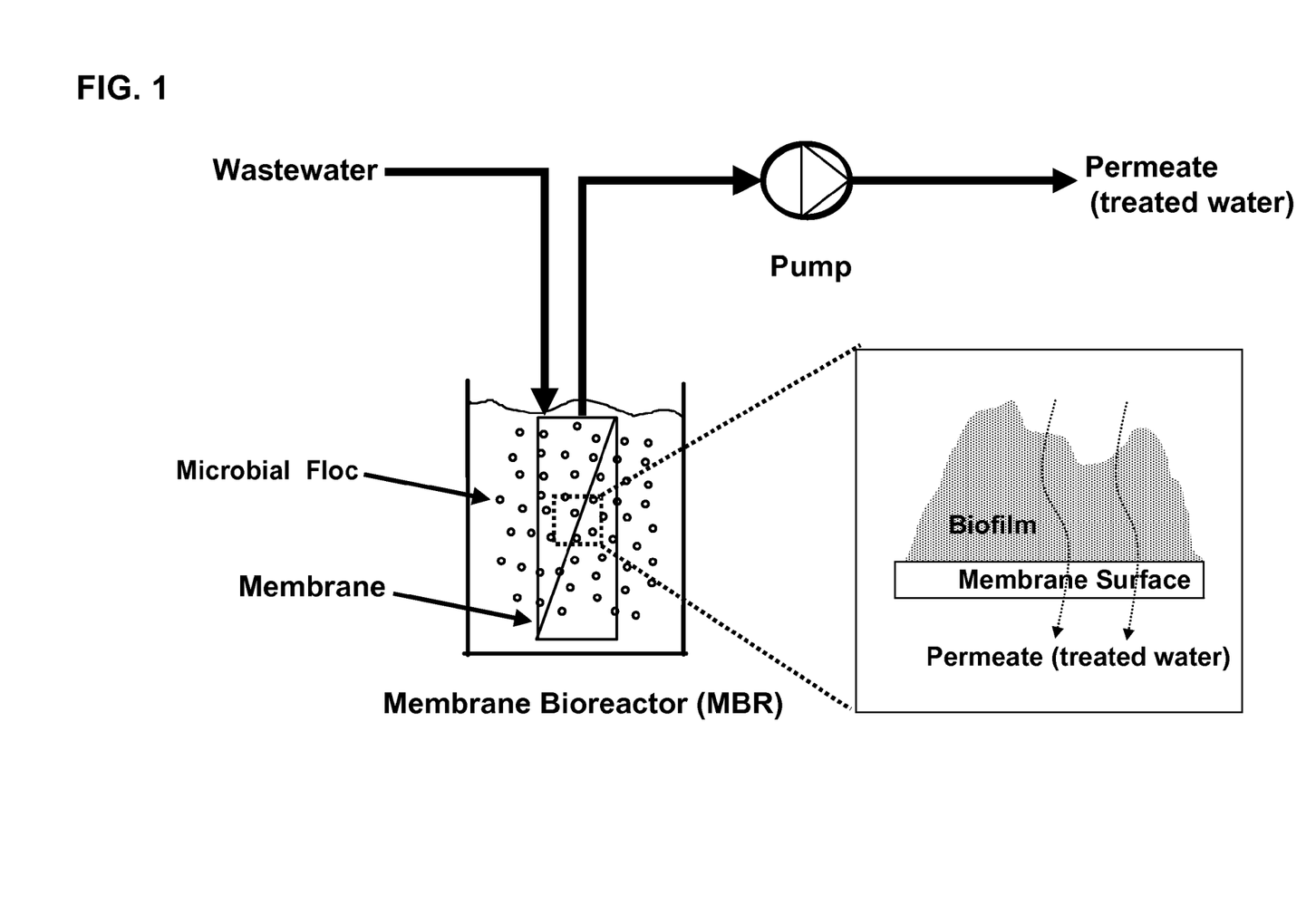
FIG. 1 is a figure illustrating biofouling which results from biofilm formation in a conventional membrane bioreactor process for advanced wastewater treatment.

However, during the operation of the MBR process, microorganisms such as bacteria, mold and algae that exist in the MBR start to attach and grow on the membrane surface ("attached growth"), and a film with a thickness of several tens of micrometers as shown in FIG. 1, that is, a biofilm is formed to cover the membrane surface. The biofilm is one of the major causes of membrane biofouling, which serves as filtration resistance to degrade the filtration performance of the membrane such as reduction of the permeability, shortening of the cleaning cycle and lifespan of the membrane, and increase of energy consumption required in filtration, thereby deteriorating the economic efficiency.

In an attempt to solve the above-described problems, various research studies have been done in the past 20 years. However, biofilm formed naturally by microorganisms on the surface of membrane could not be completely removed by conventional physical (e.g., aeration) and chemical means (e.g., coagulation by injection of polymeric coagulant), so that a satisfactory solution related to prevention and control of the biofouling has not been suggested. The outstanding biofouling problem in the MBR process is attributed to the lack of technical consideration and understanding of features of microorganisms in the reactor that directly and indirectly affect biofouling.

It is not easy to remove the biofilm which is a major factor of biofouling of the MBR because the biofilm has high resistance even in external physical and chemical shocks. As a result, although several techniques for inhibiting biofouling by the conventional physical and chemical methods are effective in the initial stage of the biofilm formation, the effect for inhibiting biofouling after maturation of the biofilm becomes degraded. In order to overcome the problem of conventional methods, new technology has been required to regulate and control characteristics of microorganisms in the reactor, specifically formation and growth of biofilm on the membrane surface.

In addition to the above MBR process, biofilm or microorganic slime is formed on a material surface by microorganisms existing in water systems ("water system" is used herein to mean equipment, facilities and process etc. using water or holding water.) such as a water tank and a water pipe of buildings and industrial facilities, thereby degrading performance of the equipment (e.g., corrosion of metal surfaces, degradation of efficiency of cooling towers, and contamination of water pipe networks by microorganisms) and deteriorating external appearance. As a result, although removal of biofilm or microorganic slime is required, there have been no solutions based on research on characteristics of microorganisms other than conventional physical/chemical methods.

Meanwhile, microorganisms tend to react to environmental change such as temperature, pH, and nutrients, to synthesize specific signal molecules and exhaust/absorb the molecules outside cells, thereby perceiving the peripheral cell density. When the cell density increases so that the concentration of the signal molecules reaches a threshold level, a specific gene expression starts. As a result, microbial group behavior is regulated, which is called a "quorum sensing phenomenon." Generally, the quorum sensing phenomenon occurs under conditions with high cell density. As examples for this phenomenon, symbiosis, virulence, competition, conjugation, antibiotic production, mobility, sporulation, biofilm formation have been reported (Fuqua et al., *Ann. Rev. Microbiol.,* 2001, Vol. 50, pp. 727~-751).

Specifically, the quorum sensing mechanism of microorganisms in the MBR process may occur more frequently and easily in the case of a biofilm state with a higher cell density than in the case of a suspended growth state with a lower cell density. Since Davies et al. reported in 1998 that the quorum sensing mechanism of *Pseudomonas aeruginosa*, which is an opportunistic pathogen, has a close relation to various features of biofilm such as the extent of its formation, the physical structure of it such as thickness and morphology, and the antibiotic resistance of the microorganism (Science, Vol. 280, pp. 295~298), research for inhibiting biofilm formation by artificial regulation of the quorum sensing mechanism has been made so as to prevent contamination of medical appliances (Baveja et al., *Biomaterials,* 2004, Vol. 50, pp. 5003~-5012) and catch of a plant diseases (Dong et al., *Nature,* 2001, Vol. 411, pp. 813~-817).

A conventional method for inhibiting biofilm formation by regulating the microorganism quorum sensing mechanism is classified into two categories. Firstly, the biofilm formation can be inhibited by injecting an antagonist that has been reported to have a similar structure to a signal molecule used in the quorum sensing mechanism and to be competitive with the signal molecule in a gene expression site. As a representative antagonist, furanone secreted by *Delisea pulchra*, which is a type of red algae, and its halogenated derivatives have been reported (Henzer et al., EMBO Journal, Vol. 22, 3803~3815). Secondly, the biofilm formation can be inhibited by an enzyme for decomposing a signal molecule used in the quorum sensing mechanism (enzyme for inhibiting biofilm formation such as an enzyme for quenching microorganism quorum sensing) or by microorganisms for producing the enzyme. For example, Xu et al. developed in 2004 a method for inhibiting biofilm formation in various surfaces by injecting a solution of acylase that is an enzyme for decomposing acyl-homoserine lactone (AHL) which is a signal molecule of Gram-negative bacteria (see U.S. Pat. No. 6,777,223).

The present inventor applied the technologies for regulating the signal molecule of microorganisms to quench the quorum sensing mechanism thereby inhibiting biofilm formation to a water system process like the MBR so as to inhibit biofouling by the formation of biofilm in micrometer scale on the material surface (e.g., membrane surface), thereby improving performance of the water system process (e.g., MBR process).

A simple method for applying the quorum sensing regulation technique to the process of water system like the MBR process involves injecting the solution of antagonist or the enzyme (e.g., enzyme for inhibiting biofilm formation) into a bioreactor with high concentration to prevent biofouling of the MBR. However, this method may cause various economic and technical problems.

First, since the antagonist or the enzyme is a soluble material, that is much smaller size than the pore size of a microfiltration membrane (0.1~0.45 µm) which is generally used in the MBR process, they tend to slip out of the MBR along with the membrane permeate. Also, while sludge is taken out periodically to keep sludge retention time (SRT) constant during the operation of the MBR, the antagonist and the enzyme may be lost along with the sludge. It is difficult to maintain effective concentration of the antagonist or the enzyme in the reactor of a MBR.

Furthermore, since temperature and pH suitable for activity, and reactive substrate are limited in the case of enzymes, it is probable that the enzyme can be inactivated in a soluble state in the MBR in which various microorganisms exist with high concentration and various contamination materials are flowed.

Because of the problems described above, a large amount of enzymes, which may be costly, should be injected periodically in order to maintain a sufficient activity of enzymes to quench the quorum sensing phenomenon in the MBR. As a result, the operational cost of a large-scale MBR may be remarkably increased.

In the case of equipment for water systems such as a water tank or a water pipe in addition to the MBR described above, when a third substance such as an enzyme with a soluble state is injected to inhibit formation of biofilm or microorganism slime, the above substance should be removed before water is finally used. This may not be economical.

Therefore, a new technique that can solve the mass loss and inactivation of the enzymes described above is required in order to prevent biofouling by using the technique for inhibiting biofilm formation with the enzyme for inhibiting biofilm formation such as the enzyme for quenching quorum sensing in the water system like the MBR process.

SUMMARY OF THE INVENTION

It is an object of the present invention to provide a new technique for inhibiting biofilm formation such as quenching microorganism quorum sensing so as to control biofouling without loss and inactivation of enzymes for inhibiting the biofilm formation when applied to the process of a water system such as the MBR process, thereby the performance of equipment or processes (e.g., the membrane filtration performance) can be improved, the enzymes can be separated and collected for recycling, and the equipment or process of a water system can be stably operated over a long period in comparison with conventional equipment or processes.

Accordingly, the present invention provides a magnetic carrier comprising an enzyme for inhibiting biofilm formation immobilized thereon so as to inhibit biofouling in a water system like the MBR process for advanced wastewater treatment, and a MBR system and biofilm inhibition method using the same.

DETAILED DESCRIPTION OF THE PREFERRED EMBODIMENTS

Figure 2:
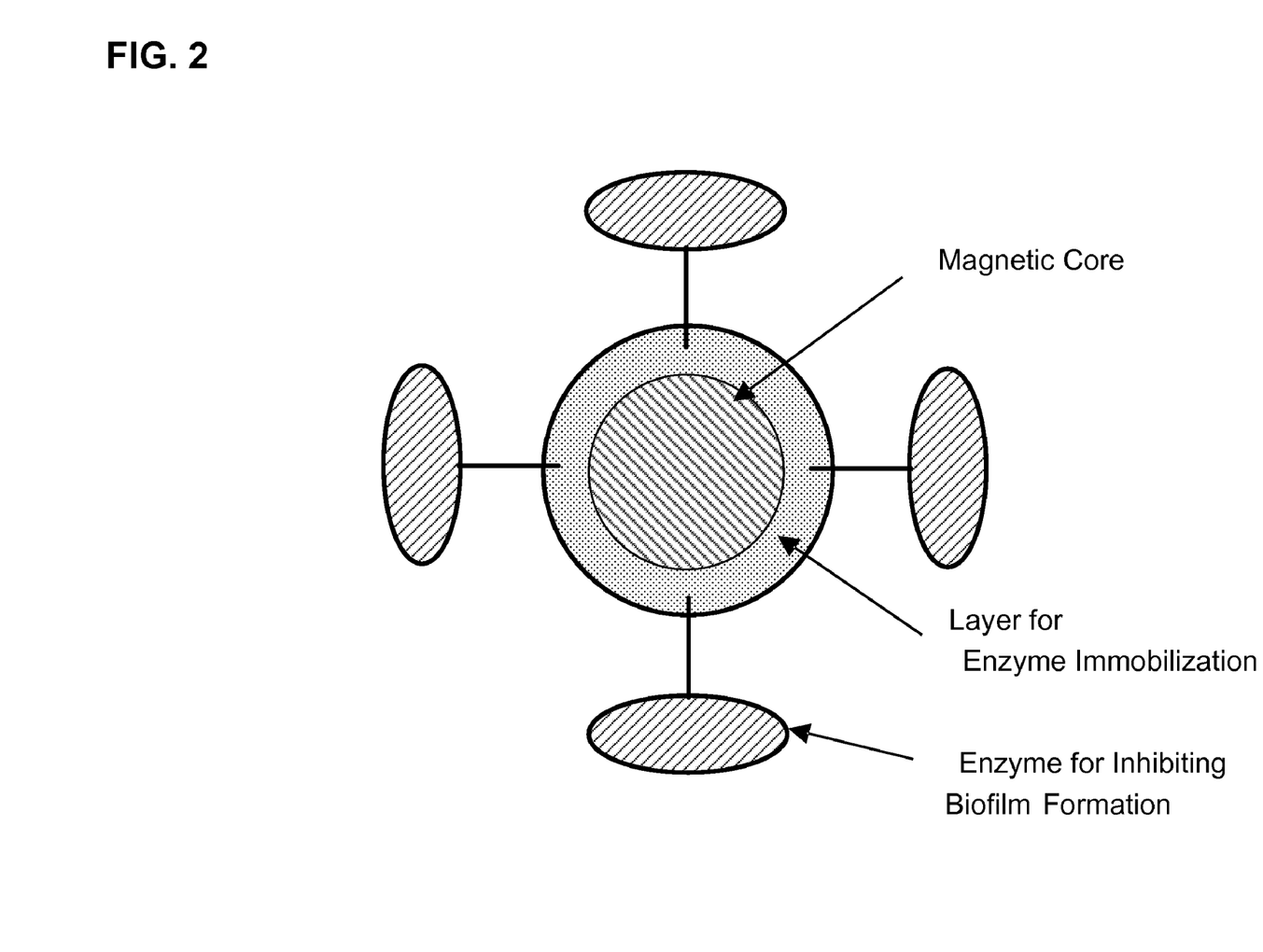
FIG. 2 is a figure illustrating a magnetic carrier comprising an enzyme for inhibiting biofilm formation immobilized thereon according to an embodiment of the present invention.
Figure 3:
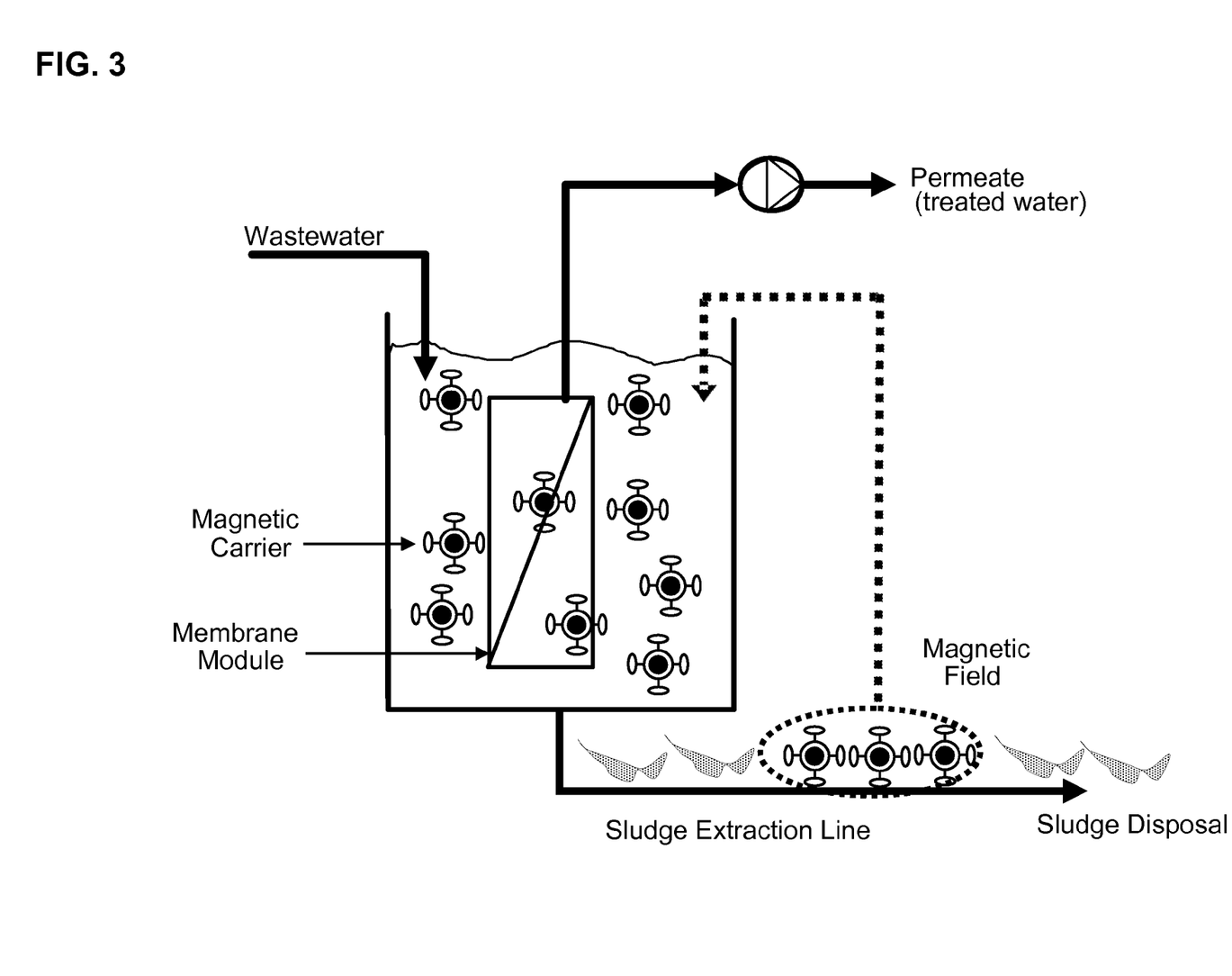
FIG. 3 is a figure illustrating a process for recycling a magnetic carrier comprising an enzyme for inhibiting biofilm formation immobilized thereon process according to an embodiment of the present invention in a membrane bioreactor.

FIG. 2 is a figure illustrating a magnetic carrier comprising an enzyme for inhibiting biofilm formation immobilized thereon according to an embodiment of the present invention. FIG. 3 is a figure illustrating a process for separating and collecting the used magnetic carrier comprising an immobi- lized enzyme according to an embodiment of the present invention using a magnetic device such as a magnet in the membrane bioreactor process.

The present invention provides a magnetic carrier that comprises a magnetic core, a layer for enzyme immobilization formed on the magnetic core, and an enzyme for inhibiting biofilm formation immobilized on the layer for enzyme immobilization.

There is no particular limitation on the magnetic core of the present invention, and any magnetic core can be used, which are given magnetism to be easily separated and collected for recycling with a magnetic device such as a magnet after it is used for a certain time in a membrane process. The magnetic core is made of at least one selected from powder, particles, beads and resin, and which are containing magnetic ingredients preferably. For example, magnetite ($Fe_3O_4$) powder, commercially available magnetic particles (SiMAG® produced by Chemicell Company), resin and beads impregnated with magnetic ingredients can be used. The size of the magnetic core can be a level or larger enough to be rejected by the microfiltration membrane (pore size: 0.1~0.45 μm) or ultrafiltration membrane (pore size: about 0.01 μm) that are generally used in a MBR. In order to collect magnetic particles easily in a large-scale engineering system, magnetic particles, resin or beads impregnated with magnetic ingredients of several tens of micrometers or larger are preferable as the magnetic core of the present invention. Further, a spherical magnetic carrier is preferable to minimize damage of the membrane surface, considering the magnetic carrier may unavoidably collide with a membrane module due to the flow of mixture in a MBR. The above resin or beads impregnated with magnetic ingredients can be commercially available products (e.g., Magnetic Ion Exchange Resin, MIEX, produced by ORICA Company), and can be fabricated directly by a cross-linking polymerization method for polymerizing monomers (e.g., styrene) mixed with magnetic ingredients.

There is no particular limitation on the feature of the layer for enzyme immobilization of the present invention, and any layer for enzyme immobilization can be formed on the magnetic core which may protect magnetic ingredients from external bacteria (corrosion inhibition), and consist of multifunctional polymers including functional groups for immobilizing enzymes. Specifically, the layer for enzyme immobilization may be formed of materials including functional groups {e.g., hydroxyl group (—OH), carboxylic acid group (—COOH), amine group (—NH$_2$)} for forming chemical covalent bonding. More specifically, the layer for enzyme immobilization comprises at least one selected from the group consisting of chitosan; 3-aminopropyltriethoxsilane; polyethyleneimine; poly(2-hydroxyethyl methacrylate (PHEMA); and polysaccharides such as cellulose, agarose and dextran. Further more specifically, chitosan is preferred because an amine group included therein can be used in enzyme immobilization, and the antibacterial feature of the chitosan prevents growth of microorganisms on the surface of the magnetic carrier, thereby inhibiting corrosion of the magnetic core.

There is no particular limitation on the enzyme for inhibiting biofilm formation of the present invention, any enzyme for inhibiting biofilm formation can be used which can prevent biofilm formation by microorganisms such as i) an enzyme for quenching quorum sensing that decomposes signal molecules used in the quorum sensing mechanism or ii) an enzyme for decomposing Extracellular Polymer Substances (EPS) consisting of the slime matrix of the biofilm. For example, the enzyme for quenching quorum sensing can be acylase and lactonase for decomposing acyl-homoserine lactone, which is a signal molecule of Gram-negative bacteria. Since the soluble product by lactonase may be re-synthesized to a signal molecule depending on pH (Camara et al., Lnacet. Infect. Dis., 2002, Vol. 2, pp. 667-676), it is preferable to use acylase. As for acylase and lactonase, other commercially available products can be used, otherwise it can be extracted and refined from microorganisms that have the above-described enzyme activity, e.g., Bacillus sp. 240B1, Bacillus strain COT1, strains of Bacillus thuringiensis, Anthrobacter sp. IBN110, Variovorax paradoxus strain VAI-C, and Ralstonia strain XJ12B. The decomposition reaction of the signal molecule by the enzymes such as lactonase and acylase is as follows.

The EPS-decomposing enzyme may include carbohydrases (e.g., cellulose, glucanase) and protease (e.g., aminopeptidase, elastase) that can decompose polysaccharides and proteins respectively, which are main ingredients of EPS. Cellulase cleaves 1,4-beta-D-glycosidic bonding of cellulose, glucanase decomposes glucane, which is a polysaccharide secreted by microorganisms, aminopeptidase hydrolyzes the terminal peptide bond at the amino end of a polypeptide, and elastase decomposes elastine or a collagen ingredient, thereby disintegrating the EPS matrix of the biofilm.

In the embodiment of the present invention, the magnetic carrier comprising an enzyme for inhibiting biofilm formation immobilized thereon can be fabricated by a method that comprises manufacturing a magnetic core, forming a layer for enzyme immobilization on the magnetic core, and immobilizing enzyme.

The method of forming a magnetic core is not limited particularly. The magnetic core may be purely composed of magnetic ingredients (e.g., magnetite), and may include magnetic ingredients impregnated during the manufacturing of particles, beads or resin to be given magnetism. The method of using particles, resin or beads impregnated with magnetic ingredients is preferable because the method facilitates following step of formation of the layer for enzyme immobilization.

Figure 4:
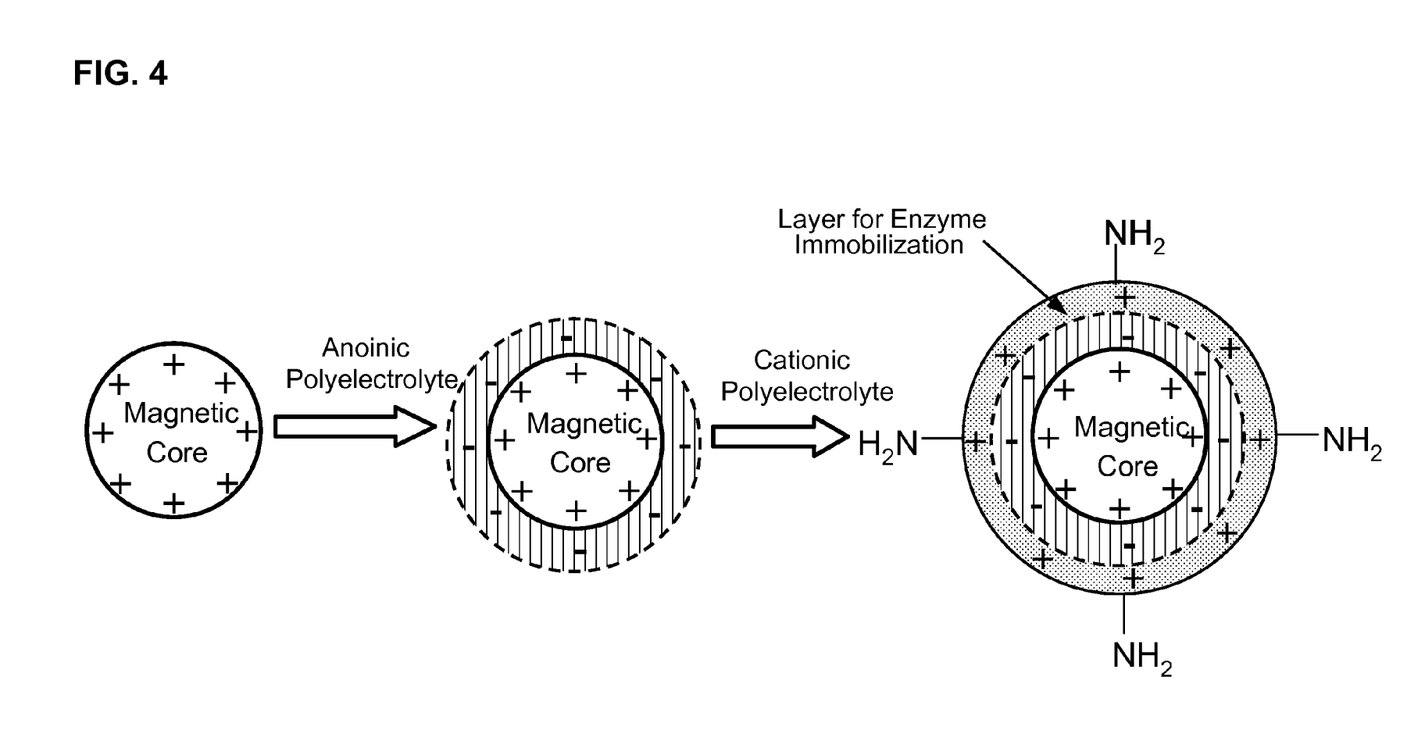
FIG. 4 is a figure illustrating a process for forming a layer for enzyme immobilization on a magnetic core by a layer-by-layer (LBL) method.

The method of forming a layer for enzyme immobilization on the magnetic core is not limited particularly, and any method of forming a layer on the core can be used. Specifically, a layer-by-layer (LBL) method using electrostatic interaction (attraction) depending on the type and characteristics of the magnetic core, or a polymerization method on the core surface can be selected. As shown in FIG. 4, in order to form a layer of chitosan (layer for immobilization), which is a cationic polyelectrolyte, on a magnetic resin carrying positive surface charge, a negative polymer layer can be formed on a magnetic resin using a LBL method by the electrostatic interaction, and cationic chitosan layers can be sequentially formed. In this case, a zeta potential of the magnetic core surface is measured so as to confirm formation of a desired layer for enzyme immobilization.

The method for immobilizing enzymes is not limited particularly, and any method capable of immobilizing an enzyme for inhibiting biofilm formation on a layer for enzyme immobilization formed on the magnetic core surface can be used. For example, after a magnetic core (e.g., resin) with a layer for enzyme immobilization formed thereon carrying positive charge is added to a solution of enzyme (e.g., acylase) of negative charge for inhibiting biofilm formation, the resultant solution is stirred under a predetermined condition, so that an acylase enzyme is immobilized (physically) on the layer for enzyme immobilization of the magnetic core surface by electrostatic interaction (attraction).

Figure 5:
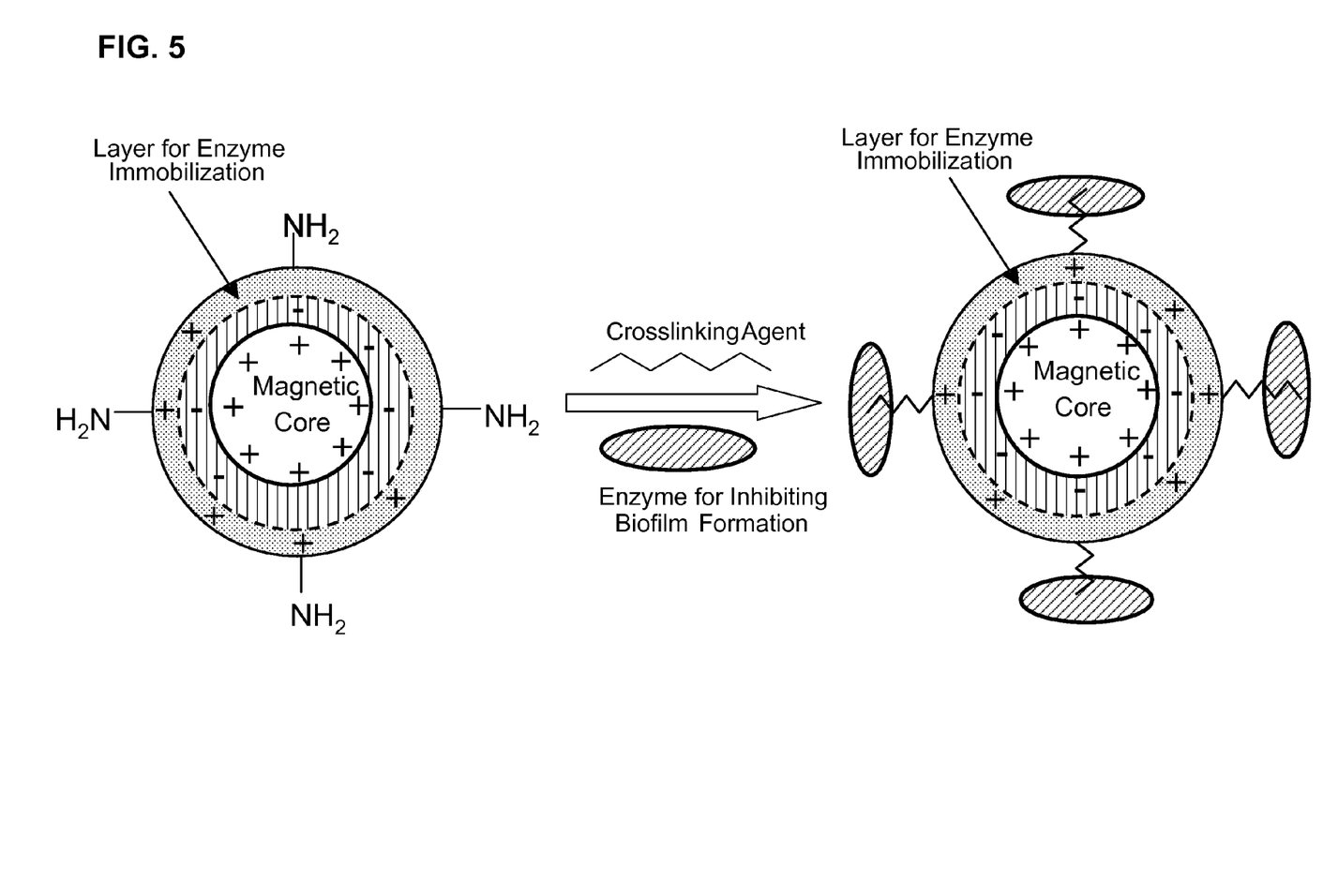
FIG. 5 is a figure illustrating a process for immobilizing an enzyme for inhibiting biofilm formation by chemical immobilization of the enzyme using a cross-linking agent on the layer for enzyme immobilization prepared in FIG. 4.

In addition to the physical immobilization, as shown in FIG. 5, a covalent bond can be formed between amine groups of the layer for enzyme immobilization (chitosan layer) and the enzyme for inhibiting biofilm formation through addition of a cross-linking agent such as glutaraldehyde, so that the enzyme can be immobilized (chemically) by a chemical method. The method of chemical immobilization for the enzyme includes various methods depending on the types of functional groups used in the formation of the covalent bond with the enzyme, and is not limited to the methods described above. For example, when a hydroxyl group is used in enzyme immobilization on the magnetic carrier surface, the hydroxyl group is activated with cyanogens bromide and S-triazine etc., thereby forming the covalent bond with the enzyme using the activated hydroxyl group. When a carboxylic acid group is used in enzyme immobilization, the enzyme is chemically immobilized using carbodiimides reagents such as 1-ethyl-3-(3-dimethylaminopropyl)-carbodiimide (EDC) and 1-cyclohexyl-3-(2-morpholino-ethyl)-carboimide (CMC). When an amine group is used in enzyme immobilization, difunctional reagents such as diimidate esters, disiocyannate, and dialdehyde in addition to glutaraldehyde described above can be used.

In order to minimize outward loss of the enzyme by immobilizing the enzyme permanently, it is preferable to use the chemical immobilization corresponding to an irreversible reaction rather than the physical immobilization corresponding to a reversible reaction.

After the magnetic carrier is prepared which comprises the enzyme for inhibiting biofilm formation by the above-described method, the magnetic carrier can be put in a reactor of a MBR system, thereby operating stably a wastewater treatment process without degrading filtration performance of the membrane over a long period. And, after the MBR process is stopped as a certain level of biofilm is formed on the membrane surface, some sludge is taken out and the magnetic carrier according to the present invention can be selectively collected using a magnet so as to be reused in the next operation.

Moreover, the magnetic carrier can be put in equipment or facilities of water systems such as a water tank or a water pipe in addition to the MBR process by a suitable method, thereby inhibiting formation of biofilm or microorganic slime by microorganisms so as to keep the performance of the equipment or facilities over a long period.

Hereinafter, the present invention will be described in detail through Preparation Examples and Examples, which is not limited herein.

PREPARATION EXAMPLE

Preparation of a Magnetic Carrier

A commercially available magnetic ion exchange resin {MIEX, produced by ORICA} was used as a magnetic core, and a layer for enzyme immobilization is formed on the magnetic core by a LBL method using electrostatic interaction (attraction).

Specifically, 20 mL of poly(sodium-4-styrene sulfonate) (PSS) solution (1% w/v), which is solution of anionic polyelectrolyte, was added in the magnetic ion exchange resin (1 g) carrying positive charge, and stirred to form a PSS layer on the magnetic resin surface. 20 mL of poly(D-glucosamin) deaceylated chitin ("chitosan") solution (1% w/v), which is solution of a cationic polyelectrolyte, was added to the resultant resin, thereby forming a layer for enzyme immobilization consisting of PSS-chitosan over the resultant resin, and an amine group of chitosan was used in the next step, chemical immobilization of the enzyme.

A zeta potential on the surface of the magnetic ion exchange resin was measured with a Zeatmeter {Zetasizer Nano Z, Malvern, UK} in each step of forming the layer for enzyme immobilization, thereby confirming formation of the layer for enzyme immobilization. Since the magnetic ion exchange resin used in the embodiment of the present invention has quaternary ammonium as a functional group of the surface site, the zeta potential has a positive value. However, when the PSS layer is formed on the surface of the magnetic resin, the zeta potential of the surface changes into a negative value. When the PSS-chitosan layer is formed on the magnetic resin by adding chitosan which is a cationic polyelectrolyte, the zeta potential of the surface changes into a positive value again. Table 1 shows the zeta potential of the surface measured in each step. Referring to Table 1, it was confirmed that the PSS-chitosan layer was formed on the magnetic resin through the change of the zeta potential.

TABLE 1

Zeta potential of the surface in each step of the LBL method

| Material (to be measured on zeta potential) | Zeta Potential (mV) |
| --- | --- |
| Magnetic resin | +16.3 |
| Magnetic resin - anionic polyelectrolyte (PSS) | −10.0 |
| Magnetic resin - anionic polyelectrolyte (PSS) - cationic polyelectrolyte(chitosan) | +24.4 |

Figure 6:
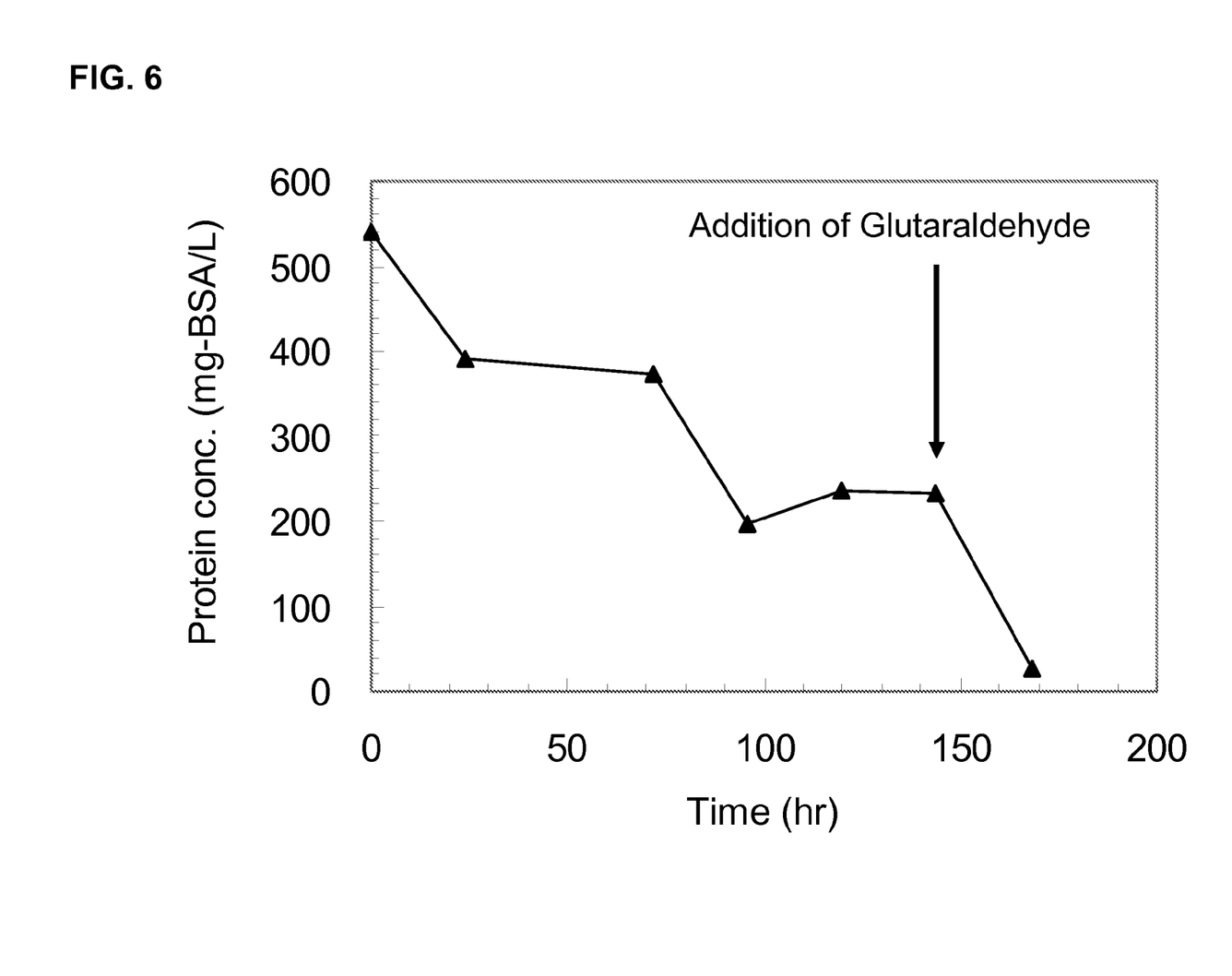
FIG. 6 is a chart illustrating the enzyme concentration while the enzyme for inhibiting biofilm formation becomes immobilized in the magnetic carrier according to an embodiment of the present invention.

After the magnetic resin (1.3 g) having a layer for enzyme immobilization was put in an acylase enzyme solution (500 ppm, 10 mL), the resulting mixture was stirred at 10° C. with 180 rpm. Since the acylase enzyme carried a negative charge and the layer for enzyme immobilization on the magnetic core carried a positive charge, the enzyme could be physically immobilized by electrostatic attraction. When the enzyme concentration of the bulk reached an equilibrium state, acylase was additionally immobilized by chemical immobilization by adding glutaraldehyde (0.05% v/v) as a cross-linking agent (see FIG. 6).

Figure 7:
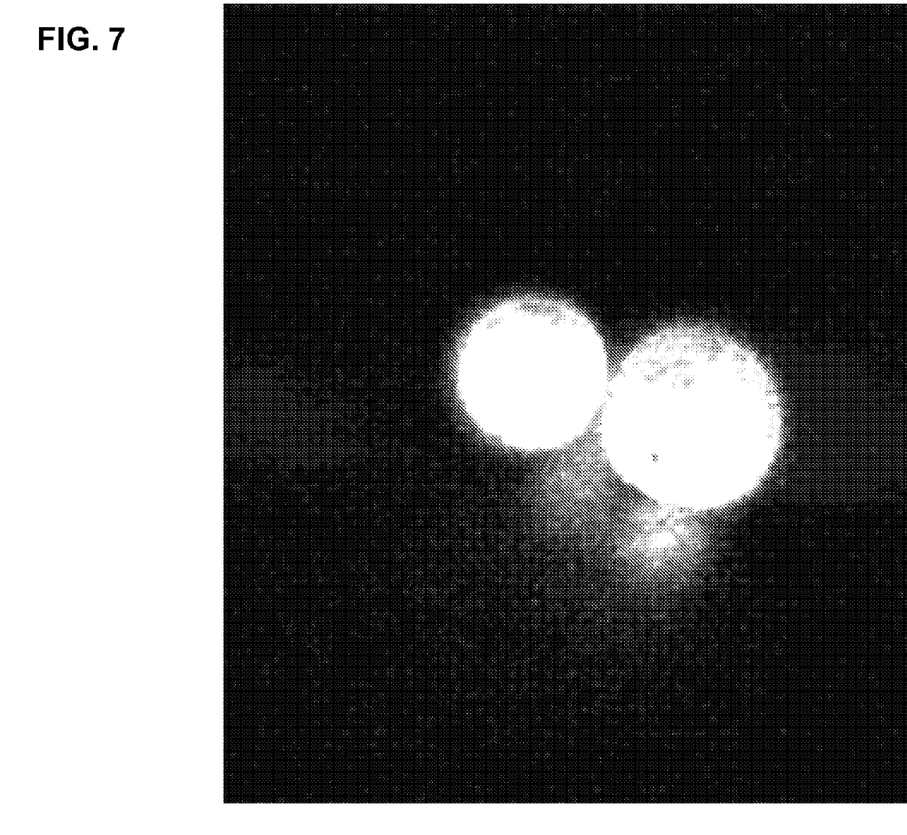
FIG. 7 is a photograph of the distribution of the enzyme for inhibiting biofilm formation immobilized chemically in the magnetic carrier according to an embodiment of the present invention taken by a Confocal Laser Scanning Microscopy.

In order to confirm space distribution of acylase immobilized on the magnetic carrier, the magnetic carrier comprising immobilized enzyme was stained with Sypro Orange, which is a fluorescence probe combining selectively with protein, and observed with a red fluorescence channel (excitation 543 nm and emission 600/50 nm) of Confocal Laser Scanning Miscroscopy (CLSM), in which the combination of the acylase enzyme (protein) with Sypro orange is detected by red fluorescence, and the location of acylase in the magnetic carrier is confirmed. As a result, as shown in FIG. 7, it was confirmed that the acylase enzyme was uniformly distributed on the surface of the magnetic carrier.

Example 1

Application in a MBR (Batch Type) Process

Figure 8:
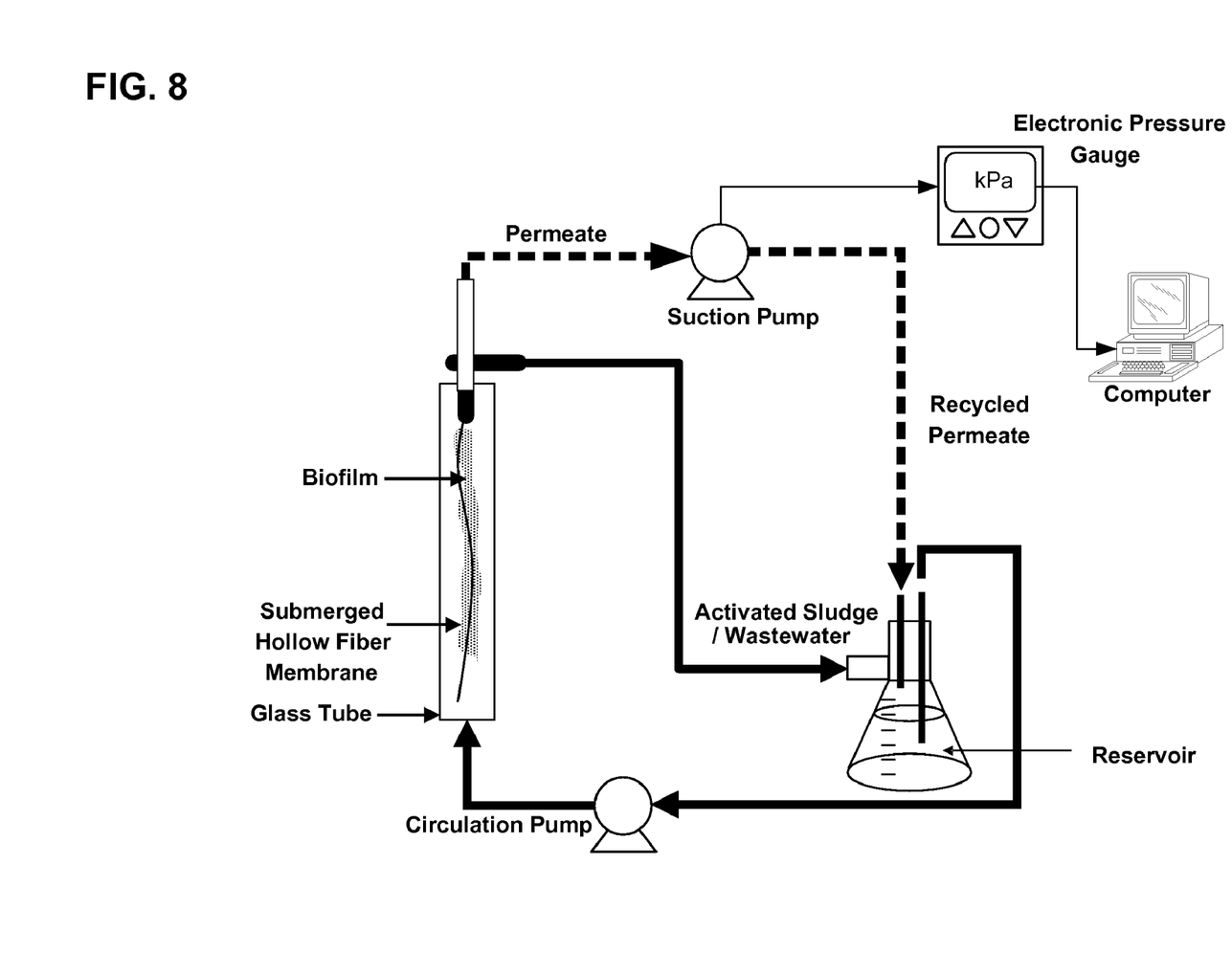
FIG. 8 is a figure illustrating a membrane bioreactor (batch type) system using the magnetic carrier according to an embodiment of the present invention.

The magnetic carrier comprising immobilized enzyme prepared from the above Preparation Example was applied to a lab scale MBR process (see FIG. 8). In order to observe the effect of biofouling alone by a biofilm formed by self-growth of the microorganism attached on the membrane surface, the MBR was operated with a batch type (total recycle method) where a microorganism layer transferred and accumulated from a suspended region to the membrane surface region in a MBR is swept away by inflow of permeate (treated water) which is circulated from a reservoir to a membrane module.

Figure 9:
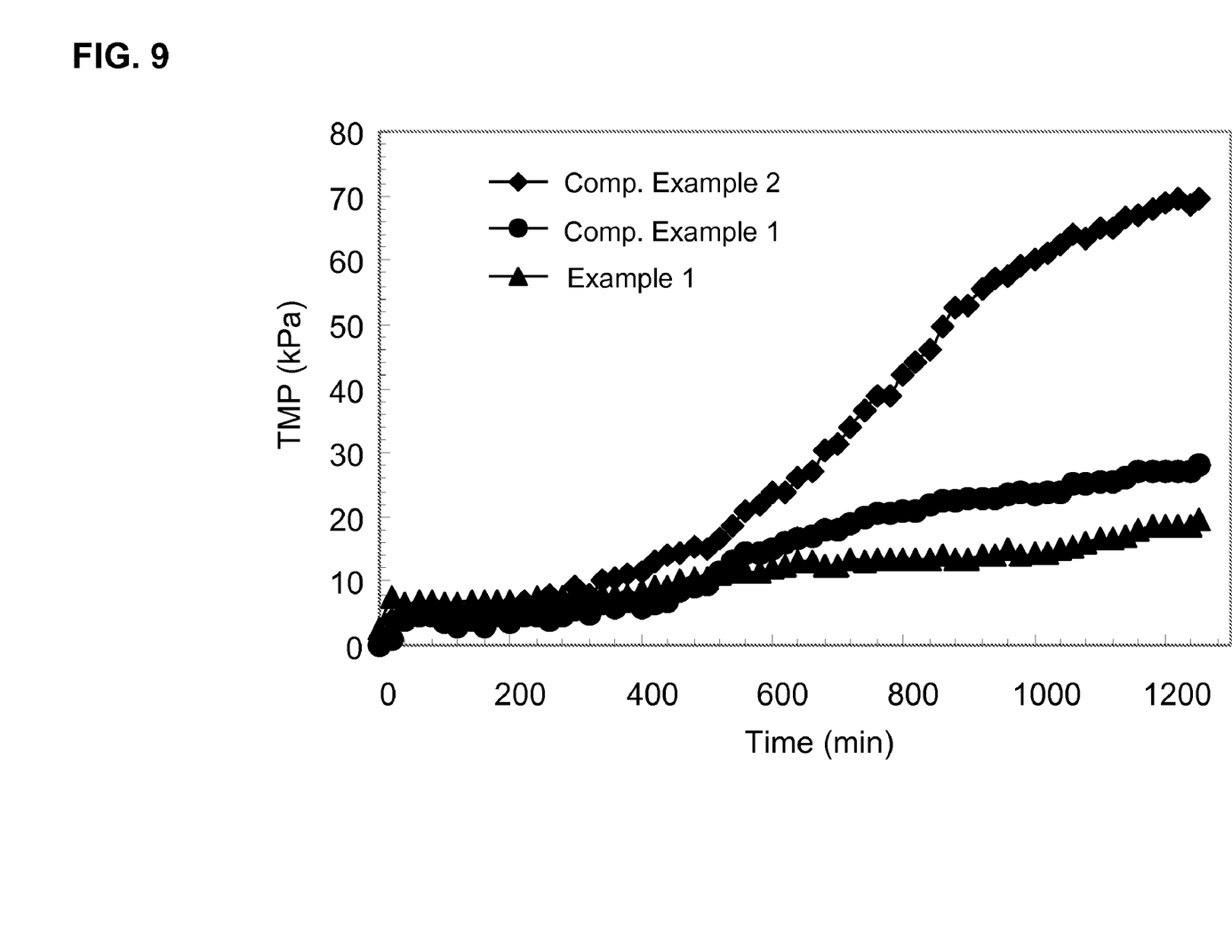
FIG. 9 is a chart illustrating the transmembrane pressure rise-up (biofouling rise-up) outlines in Example 1 and Comparative Examples 1~2 of the membrane bioreactor (batch type) process according to an embodiment of the present invention.

Specifically, after activated sludge was inoculated to synthetic wastewater in a 150 mL reservoir (flask), the synthetic wastewater and the activated sludge were transferred and circulated through a pump into a glass tube (hollow fiber module) where a hollow fiber membrane was vertically included. The filtration was performed with a batch type (total recycle method) where the permeate was filtered through the membrane with a predetermined flow rate using a suction pump, and flowed in the reservoir again. The synthetic wastewater using glucose as a main carbon source had a chemical oxygen demand (COD) of 1,000 ppm. The activated sludge was collected from Si-Hwa sewage disposal plant (located in Gyeongki-do, Korea) and acclimated sufficiently to the used synthetic wastewater. As for the membrane, a submerged hollow fiber ultrafiltration membrane (ZeeWeed500™ produced by GE-Zenon Company, diameter: 0.04 μm) was used. The MBR was operated with a constant flux, 15 LMH (l·m$^{-2}$·hr$^{-1}$), of permeate penetrating the membrane. The magnetic carrier of the present invention was put into the MBR so that the concentration of the acylase enzyme was to be 10 ppm. As the operation proceeded, the biofilm was formed on the membrane surface, which degraded permeability of the membrane due to increase of biofouling. The degree of the biofouling was represented with a value of transmembrane pressure (TMP). As the TMP increases, the degree of biofouling deepens. As a result of the operation for a duration of 1,200 minutes, the TMP was no more than 15 kPa (see FIG. 9).

Comparative Example 1

The same procedure from Example 1 was repeated except injecting the acylase enzyme, with a solution state not immobilized state into the MBR so that the concentration of acylase in the reactor was to be 10 ppm. As a result of the operation for a duration of 1,200 minutes, the TMP reached 22 kPa.

Comparative Example 2

The same procedure from Example 1 was repeated except the magnetic carrier according to the present invention where the acylase enzyme was immobilized was not injected into the MBR. As a result of the operation for a duration of 1,200 minutes, the TMP reached 70 kPa.

Example 2

Application in a MBR (Continuous Type) Process

Figure 10:
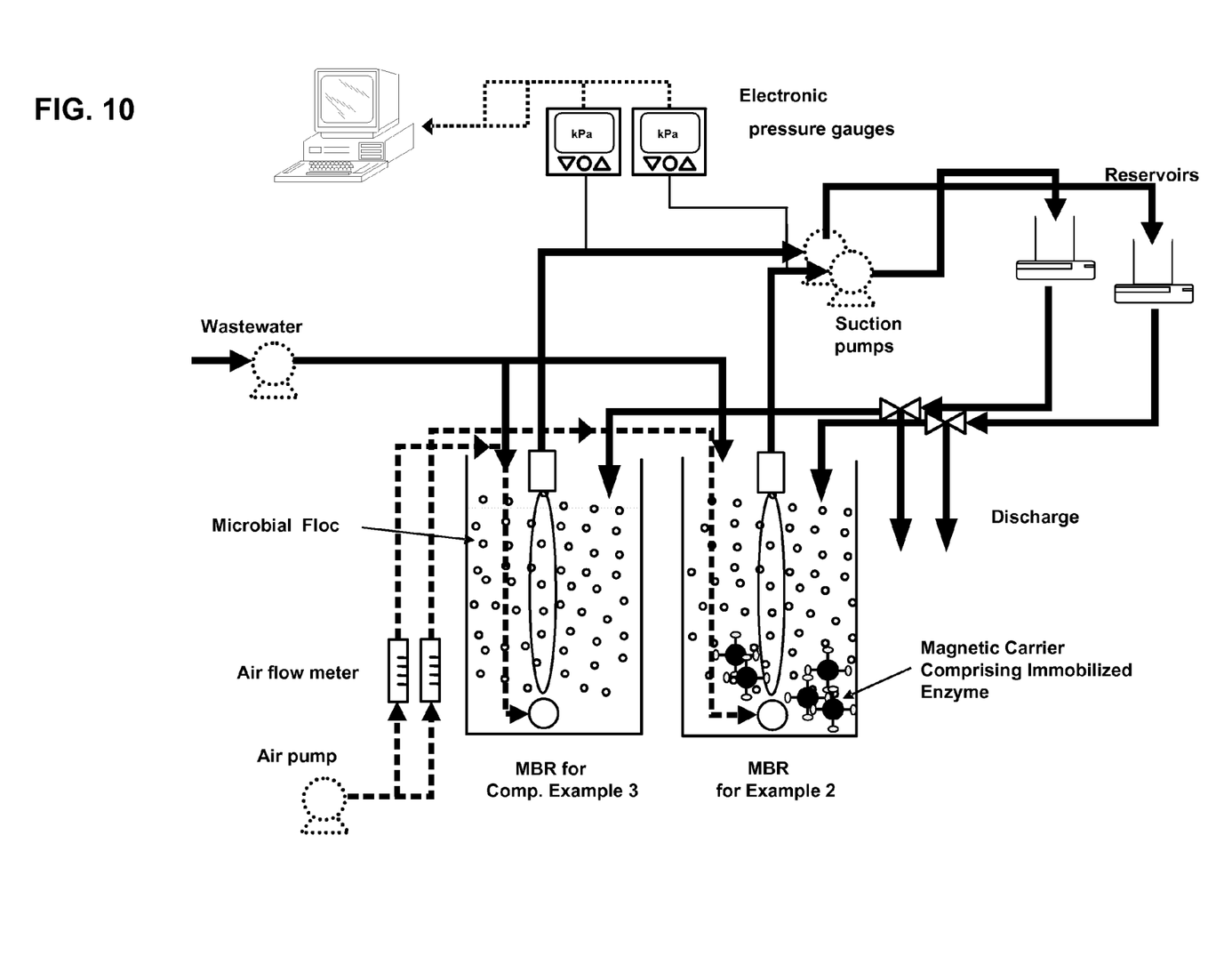
FIG. 10 is a figure illustrating a membrane bioreactor (continuous operation type) system using the magnetic carrier according to an embodiment of the present invention.

The magnetic carrier comprising immobilized enzyme prepared from the above Preparation Example was applied in a laboratory-scaled MBR process of continuous type (see FIG. 10). Example 2 was performed to simulate an actual MBR process where flow of wastewater and filtration of treated water were continuously performed.

The same synthetic wastewater and activated sludge as those of Example 1 were used. The magnetic carrier comprising immobilized enzyme (0.5 g) of the present invention was put into a reactor which has a working volume of 1 L and mixed liquor suspended solids (MLSS) of 26,000 (±1,300 mg/L), so that enzyme concentration in MBR reactor is to be 8.3 ppm. While the synthetic wastewater flowed into a reactor at a flow rate of 100 ml/hr {hydraulic retention time (HRT): 10 hr}, the synthetic wastewater was filtered with a constant flux, 15 LMH (l·m$^{-2}$·hr$^{-1}$), through a hollow fiber membrane module {membrane area: 0.008 m$^2$, pore size: 0.04 μm, ZeeWeed 500™, GE-Zenon USA} submerged in the reactor. The permeate (treated water) was transferred to a reservoir. About 20 mL of sludge per day was extracted from the reactor, thereby maintaining the solids retention time (SRT) to be 50 days. In the sludge extraction line of a reactor, a magnetic retriever was installed to collect the magnetic carrier comprising immobilized enzyme according to the present invention extracted along with the sludge. The collected magnetic carrier was re-injected into the reactor.

Figure 11:
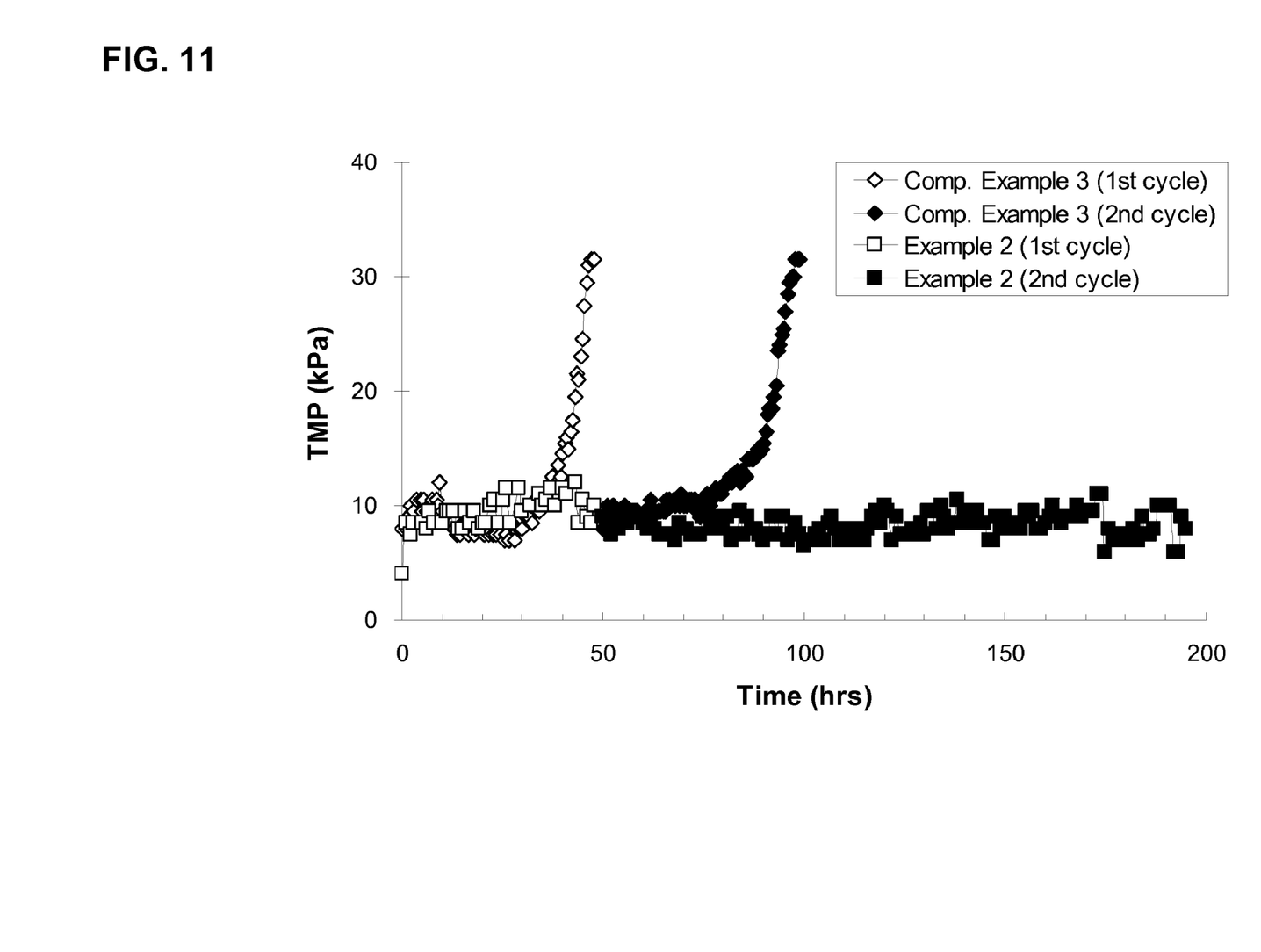
FIG. 11 is a chart illustrating the transmembrane pressure rise-up (biofouling rise-up) outlines in Example 2 and Comparative Example 3 of the membrane bioreactor (continuous operation) process according to an embodiment of the present invention.

An electronic pressure gauge was installed in the downstream of a membrane module so as to record change of TMP of the MBR during continuous operation. FIG. 11 shows the results. In the continuous MBR process where the magnetic carrier comprising immobilized enzyme was injected, the TMP was shown to hardly increase from its initial value. After 48 hours of continuous operation, the membrane module of the reactor was replaced with a new one, and the operation restarted. Even after further operation for 6 days, there was a negligible change to the TMP.

In an actual operation of the MBR process, the treatment quality of treated water as well as the increase of the TMP by biofouling is an important performance evaluation index. The COD of treated water of the MBR in the above operation was measured as 13.2 (±4.5) mg/L. It was confirmed that the microbial quorum sensing mechanism, which occurs in the magnetic carrier comprising immobilized enzyme of the present invention for alleviating the biofouling, had no negative side effect upon microbial activity related to removal of organisms of wastewater.

Meanwhile, the regulation of gene transcription for microorganisms through the quorum sensing mechanism has a close relation to a physiological state of the microorganisms. It has been reported that the physiological state of the microorganisms affects the secreting characteristic of soluble microbial products (SMP) and EPS consisting of the biofilm, and determines the degree of biofouling in the MBR (Kim et al., *Separation science and technology*, 2006, Vol. 41, pp. 1213-1230; Chang et al., *Desalination*, 1998, Vol. 120, pp. 221-233). Based on this point, the present inventor analyzed SMP and EPS of the reactor to observe change of physiological feature for microorganism by the magnetic carrier comprising immobilized enzyme. According to the analysis, when the magnetic carrier comprising immobilized enzyme of the present invention is used, it is considered that the secretion of SMP and EPS for microorganisms is reduced and regulated, so that the biofouling of the MBR is reduced (that is, the permeability is improved).

Comparative Example 3

The same procedure from Example 2 was operated at the same time as shown in FIG. 10 except that the magnetic carrier comprising immobilized enzyme was not injected into the MBR, and mixed liquor suspended solids (MLSS) was 24,000 (±3,500 mg/L) slightly different from Example 2 {The slight difference of MLSS was not intentional, but the difference was negligible not to have an substantial effect on the present invention.}. As a result of the operation for a duration of 48 hours, the TMP reached 30 kPa. At that time the membrane module was replaced with a new one, and the operation restarted. As a result of the further operation for about 2 days, the TMP reached 30 kPa.

The COD of treated water of the MBR was shown to be 16.9 (±5.7) mg/L.

As described above, a magnetic carrier comprising an enzyme for inhibiting biofilm formation immobilized thereon according to the present invention inhibits biofouling of the membrane by a mechanism for inhibiting biofilm formation on the membrane surface by decomposing signal molecules of microorganisms, thereby improving membrane filtration performance. Since the enzymes can be separated and collected with a magnetic field (magnetism) if necessary, a wastewater treatment process can be operated stably and efficiently over a long period. Specifically, the magnetic carrier according to the present invention can be properly used in a large-scale engineering system where biofouling prevention is important.

What is claimed is:

1. A magnetic carrier for inhibiting biofilm formation comprising a magnetic core, a layer for enzyme immobilization formed on the magnetic core, and an enzyme for inhibiting biofilm formation immobilized on the layer for enzyme immobilization.

2. The magnetic carrier for inhibiting biofilm formation according to claim 1, wherein the magnetic core is made of powder, particles, beads or resin containing magnetic ingredients.

3. The magnetic carrier for inhibiting biofilm formation according to claim 1, wherein the layer for enzyme immobilization is formed on the magnetic core by electrostatic interaction.

4. The magnetic carrier for inhibiting biofilm formation according to claim 1, wherein the layer for enzyme immobilization comprises at least one selected from the group consisting of chitosan, 3-aminopropyltriethoxsilane, polyethyleneimine, poly(2-hydroxyethyl metacrylate (PHEMA), cellulose, agarose, and dextran.

5. The magnetic carrier for inhibiting biofilm formation according to claim 1, wherein the enzyme for inhibiting biofilm formation is an enzyme for quenching quorum sensing or an enzyme for decomposing extracellular polymeric substances (EPS).

6. The magnetic carrier for inhibiting biofilm formation according to claim 1, wherein the enzyme for inhibiting biofilm formation is physically combined with the layer for enzyme immobilization by electrostatic interaction.

7. The magnetic carrier for inhibiting biofilm formation according to claim 1, wherein the enzyme for inhibiting biofilm formation is chemically combined with the layer for enzyme immobilization by cross-linking.

8. The magnetic carrier for inhibiting biofilm formation according to claim 5, wherein the enzyme for quenching quorum sensing is acylase or lactonase.

9. A membrane bioreactor system comprising a membrane module and the magnetic carrier of claim 1, which is put in water to be treated.

10. A method for inhibiting biofilm formation on a material surface in a water system using the magnetic carrier for inhibiting biofilm formation described in claim 1.

* * * * *